United States Patent [19]
Wood

[11] Patent Number: 6,019,791
[45] Date of Patent: Feb. 1, 2000

[54] BUTTRESS FOR CARDIAC VALVE RECONSTRUCTION

[76] Inventor: Alfred E. Wood, Wynberg, Belgrave Road, Monkstown, County Dublin, Ireland

[21] Appl. No.: 09/000,059
[22] PCT Filed: Jul. 17, 1996
[86] PCT No.: PCT/IE96/00041
  § 371 Date: Jan. 12, 1998
  § 102(e) Date: Jan. 12, 1998
[87] PCT Pub. No.: WO97/03625
  PCT Pub. Date: Feb. 6, 1997

[30] Foreign Application Priority Data

Jul. 17, 1995 [IE] Ireland ..................... 950546

[51] Int. Cl.[7] .................................. A61F 2/24
[52] U.S. Cl. ............................................. 623/2
[58] Field of Search ............................ 623/2, 900

[56] References Cited

U.S. PATENT DOCUMENTS

| | | | |
|---|---|---|---|
| 4,042,979 | 8/1977 | Angell | 623/2 |
| 4,055,861 | 11/1977 | Carpentier et al. | 623/2 |
| 4,164,046 | 8/1979 | Cooley | 623/2 |
| 5,290,300 | 3/1994 | Cosgrove et al. | 606/148 |
| 5,397,348 | 3/1995 | Campbell et al. | 623/2 |
| 5,522,884 | 6/1996 | Wright | 623/2 |

FOREIGN PATENT DOCUMENTS

0338994A1  10/1989  European Pat. Off. .
WO 93/15690  8/1993  WIPO .

OTHER PUBLICATIONS

Duran et al., The Annals of Thoracic Surgery, (22) 5, 458–463, Nov. 1976.
Melo et al., The Journal of Thoracic and Cardiovascular Surgery, (110) 5, 1333–1337, Nov. 1995.

Primary Examiner—David H. Willse
Attorney, Agent, or Firm—Quarles & Brady

[57] ABSTRACT

A buttress for cardiac valve reconstruction comprises an elongate member formed from two superimposed layers of a fabric. The layers are fastened together by longitudinally extending seams having inwardly extending opposing selvedges. The elongate member fits part-annularly against the base of the cusps of the cardiac valve. The fabric is longitudinally extendable to 105–150% of its non-extended length. An apparatus for cardiac valve reconstruction comprises a holder, including a buttress receiving area; and a buttress comprising a part-annularly shaped elongate member formed from a fabric. The buttress is removably mounted onto the buttress receiving area of the holder in an extended condition, the extended condition being 105–150% of the non-extended length of the elongate member. The buttress and apparatus can be used in the reconstruction of mitral and tricuspid cardiac valves.

28 Claims, 5 Drawing Sheets

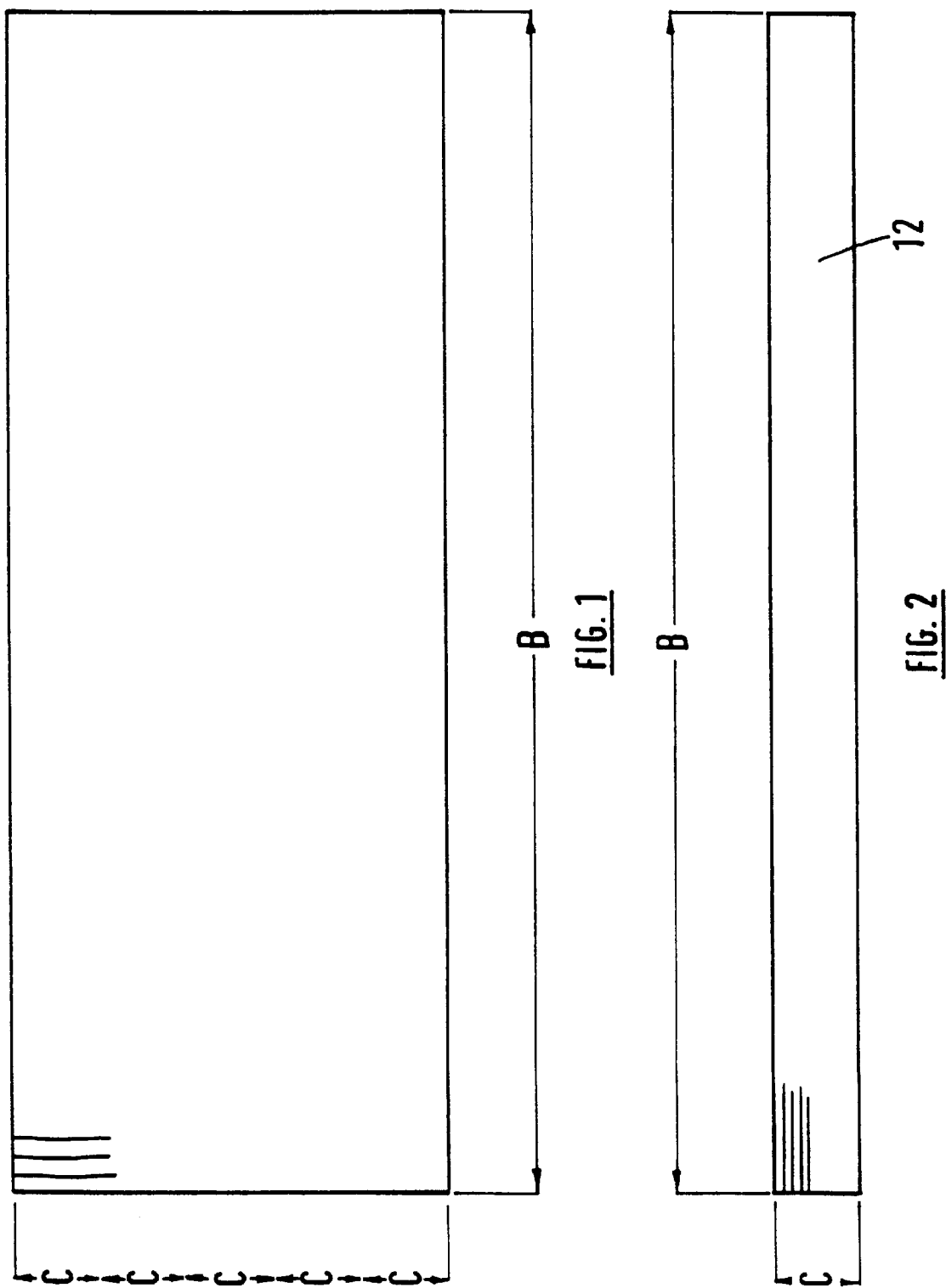

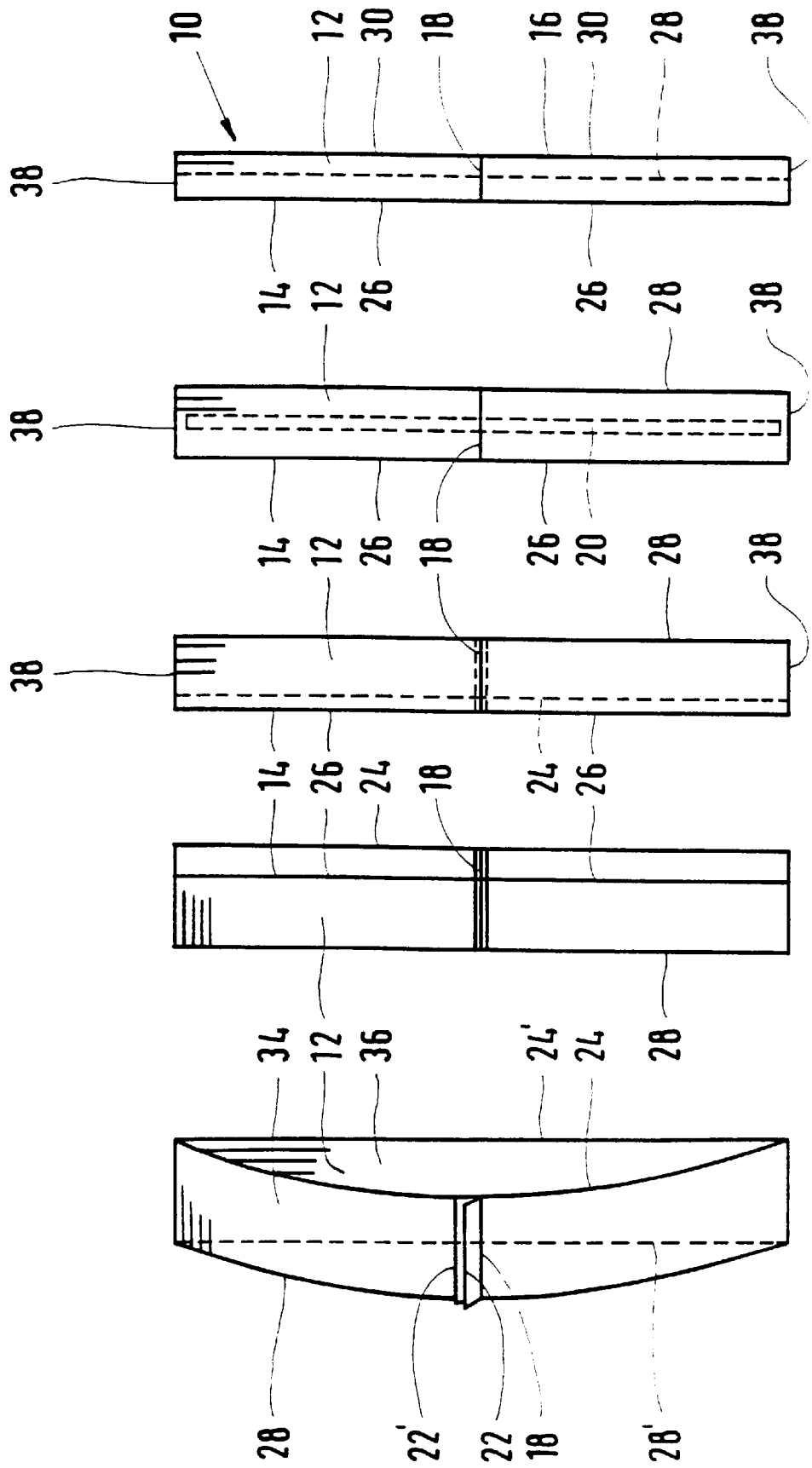

BUTTRESS FOR CARDIAC VALVE RECONSTRUCTION

The present invention relates to a buttress for cardiac valve reconstruction of atrioventricular cardiac valves.

The mitral and tricuspid valves are located in the left and right atrioventricular openings, respectively, of the heart and serve to prevent regurgitation of blood from the ventricle into the atrium when the ventricle contracts during systole.

The mitral valve, which is surrounded by a dense fibrous ring known as the annulus, comprises two valve cusps or leaflets of unequal size, the large or anterior leaflet adjacent the aortic opening and the smaller posterior leaflet. The line at which the leaflets come together is called the commissure.

The tricuspid valve comprises three leaflets, usually referred to as the anterior, posterior and septal cusps, which are attached to a fibrous ring known as the annulus.

The mitral valve is subjected to significantly higher back pressure than the tricuspid valve. Accordingly, it is more common to require surgery to repair a mitral valve than a tricuspid valve and, therefore, the discussion herein is primarily concerned with mitral valve reconstruction. However, it will be understood that the same principles apply in respect of both mitral and tricuspid valve reconstruction.

The most common defect leading to mitral valve dysfunction is a dilation of the posterior two-thirds of the annulus which corresponds to the posterior leaflet. Thus, in repairing a mitral valve, it is sometimes necessary to reduce the annulus in its physiological dimensions by repairing the dilated posterior two-thirds thereof. Similar concepts apply to the correction of tricuspid valve defects.

In a normal heart, the mitral and tricuspid annuli move in a dynamic and non-planar way with each cardiac cycle. The circumference of the mitral and tricuspid annuli reduce during systole, so that their respective surface areas reduce by about 20–250%, and then enlarge correspondingly during diastole. The movement of each annulus, which is non-planar, is difficult to describe but would be similar to a pitching, yawing, rolling or rotation motion. All the components of each annulus do not necessarily move to the same degree.

One solution for severe atrioventricular valve dysfunction is total valve replacement. However, it is generally agreed that cardiac valve reconstruction by annuloplasty is preferable to valve replacement.

One such known annuloplasty buttress comprises a rigid annular or part-annular member which is dimensioned to fit against the base of the valve leaflets and is secured in place by sutures. Known rigid annular (or closed) annuloplasty rings affect the movement of the annulus by preventing normal movement, specifically, by restricting it to planar movement. This reduces ventricular function and, if the ventricle is compromised already, is likely to reduce its efficiency further. Another disadvantage of such non-planar movement is a tendency to force the rigid ring to dehisce or be torn loose from the annulus by the securing sutures being pulled through the tissue. This happens as a result of the stress caused by restraining the annulus from undergoing normal physiological changes during each cardiac cycle. Furthermore, the closed nature of a rigid ring prevents the natural change in the circumference of the annulus, in particular, that which occurs during diastole (the relaxation phase of the cardiac cycle) when the surface area of the mitral and tricuspid valve orifices increase by 20–25%. In addition, the rigid closed ring, in particular, limits the movement of the anterior mitral leaflet in the inter-trigonal region. This effectively limits the ability of the closed ring system and, at high flow rates across the mitral or tricuspid valve, is likely to produce obstruction/stenosis.

Known rigid part-annular (or open) rings suffer less from the problems of rigid closed rings. However, their inherent rigidity restricts normal movement of the annulus and, thereby, depresses ventricular function. Furthermore, because of the restricted non-planar movement of the annulus during each cardiac cycle, dehiscence at either end of the ring would be more likely to occur due to the excessive strains that would be placed on the retaining sutures in those areas.

Thus, as a result of the known disadvantages of rigid annuloplasty rings, a flexible closed ring was devised for use in atrioventricular annuloplasty. The structural properties of the material required for the flexible closed ring are inertness and non-biodegradability. The material should also permit good, but not excessive, tissue in-growth since excessive tissue in-growth would convert the flexible nature of the device into a rigid device. It was expected that a flexible ring would permit normal movement of the annulus during the cardiac cycle. This should allow the heart to function in a more natural manner and, in addition, should decrease the tendency of dehiscence because the stress forces in any particular part of the ring would be reduced.

A subsequent modification of the flexible closed ring involved the incorporation of a traction thread which passes through the interior of the ring, with both ends exiting the ring a short distance apart. Such a ring, once implanted, can be reduced in circumferential size, by pulling on the traction thread to contract the ring either symmetrically, by pulling both ends of the traction thread the same amount, or asymmetrically, by pulling one end more than the other. Once the desired ring circumferential size has been achieved, the ends of the traction thread are then tied off.

A flexible closed ring has less device-related problems such as haemolysis (red cell damage), or shear damage across the device than a rigid ring. Furthermore, the flexible nature of the flexible closed ring interferes less with ventricular function than the rigid systems described above.

Unfortunately, each of such known closed flexible rings fail to restore normal heart valve function since, as mentioned above, the most common mitral heart valve defect is a dilation of the posterior two-thirds of the valve annulus and an accompanying loss of the normal shape of the valve. In such circumstances, the natural tendency of a damaged valve is to re-assume its unnatural shape and one of the disadvantages of known flexible closed rings is that they allow too much movement of the valve annulus, thereby failing to support the damaged annulus sufficiently to restore and maintain a normal annular shape. Furthermore, known flexible closed rings are liable to reduce the orifice area to a greater extent and make it even smaller than the actual ring implanted, due to a "crimping" or buckling effect of sutures as they are tied down, which effectively creates stenosis or obstruction. The known flexible closed rings using traction or draw strings suffer from the same problem as the simple closed flexible rings, in that it is very easy to reduce the orifice size of the mitral ring excessively, thus creating stenosis. In addition, they also leave a cumbersome suture prolapsing, which can specifically be a site for infection and/or haemolysis.

Whilst this discussion is primarily directed to mitral valve reconstruction, similar considerations apply for tricuspid valve reconstruction but the annuloplasty buttress will need to be larger to accommodate the correspondingly larger dimensions of the tricuspid annulus.

It is an object of the present invention to provide a flexible buttress which permits normal anatomical movement of the annulus during the cardiac cycle, while providing sufficient support to the damaged annulus, in order to maintain its normal physiological shape and, thereby, ensure the proper functioning of the cardiac valve.

According to the present invention there is provided a buttress for cardiac valve reconstruction, the buttress comprising an elongate member formed from a fabric bendable, in use, into an open substantially ring-shaped configuration dimensioned to fit against the base of the cusps of the cardiac valve.

It has surprisingly been found that such a buttress according to the invention, which is substantially "C"-shaped, permits both normal non-planar annular movement and expansion/contraction of the annular circumference during the cardiac cycle, whilst, at the same time, restoring the damaged annulus towards its normal physiological shape.

Preferably, the arcuate spacing between the free ends of the elongate member is more than one quarter of the unextended length of the elongate member.

More preferably, the buttress is adapted for mitral valve reconstruction and, in use, fits against at least the base of the posterior mitral leaflet. Even more preferably, the unextended length of the elongate member approximates four times the maximum depth of the anterior mitral leaflet, from the base of the anterior leaflet to the commissure with the posterior mitral leaflet.

Alternatively, the buttress is adapted for tricuspid valve reconstruction and, in use, fits against at least the base of the anterior tricuspid leaflet. Advantageously, the fabric is adapted to be both longitudinally and transversely expandable. More advantageously, the fabric is adapted to be longitudinally and transversely expandable by the provision of, on one side, longitudinally extending ribs and, on the reverse side, transversely extending ribs.

Even more advantageously, the fabric is woven or knitted from polymerised tetrafluoroethylene.

More preferably, the fabric is adapted to be longitudinally extendable to no more than 150%, preferably no more than 125%, more preferably about 105–108% of the length of the elongate member in a non-extended condition.

Even more preferably, the elongate member is substantially cuboid-shaped.

Advantageously, the elongate member comprises two superimposed layers of the fabric, which layers are fastened together by longitudinally extending seams, having inwardly extending, opposing selvedges.

More advantageously, the elongate member comprises a length of fabric folded at each end in a reflex manner, to form the two superimposed layers. Alternatively, the elongate member comprises two superimposed lengths of fabric.

Preferably, the buttress is impregnated with a radiopaque material comprising an inert, water insoluble, heavy metal compound, preferably barium sulphate or titanium dioxide. Alternatively, a radiopaque filament is provided within the buttress, the radiopaque filament including an inert, water insoluble heavy metal compound such as, for example, barium sulphate or titanium dioxide. This renders the buttress radiopaque and allows it to be observed in vivo radiologically and under fluoroscopy. In addition, from a safety point of view, if the buttress were to migrate, this would allow the buttress to be readily located.

Several embodiments of the invention will now be described, by way of example, with reference to the accompanying drawings in which:

FIG. 1 is a plan view of a fabric column;

FIG. 2 is a plan view of a cuff from the fabric column of FIG. 1;

FIG. 3 is a perspective view and FIGS. 4–7 are plan views of sequential steps in a process for the manufacture of a buttress according to a first embodiment of the present invention;

The invention will now be illustrated in the following Examples and by reference to the accompanying drawings, in which similar reference numbers have been used to indicate like parts.

EXAMPLE 1

Figure 8:
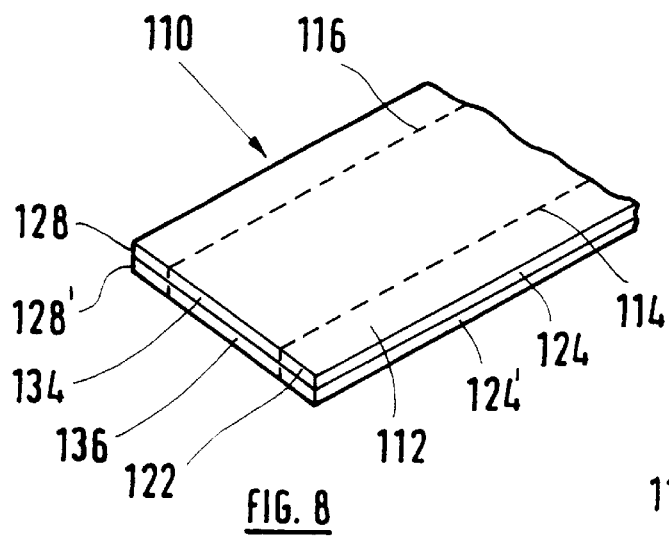
FIGS. 8 and 9 are perspective views of steps involved in the manufacture of a buttress according to a second embodiment of the present invention.

The following procedure describes steps involved in the manufacture of a buttress generally indicated as 10 according to the present invention. It will be appreciated that all these steps should be carried out on a designated clean work surface in a clean environment area.

The buttress 10 according to the invention is manufactured according to the procedures set out hereinbelow, with reference to the sequential steps illustrated in FIGS. 1–7 of the accompanying drawings.

The finished buttress 10 according to the invention, as illustrated in FIG. 7 of the accompanying drawings, comprises an elongate member 12 which is substantially cuboid-shaped.

The buttress 10 according to the invention is formed by longitudinally fastening two layers of fabric 34, 36 together, by means of second and third seams 14, 16 respectively. The free ends 22,22' of the fabric are fastened together by a transversely extending first seam 18.

The buttress 10 according to the invention may be rendered radiopaque by either impregnating the fabric with a radiopaque material (not shown) or by providing a radiopaque material (20) in the form of a filament within the lumin of the buttress 10. It will be appreciated that the buttress 10 according to the invention, in itself, is not necessarily radiopaque and it may be desirable to render it radiopaque, in order to be able to observe, in vivo, the movement of the annulus during the cardiac cycle and the location of the buttress 10 within the annulus.

TABLE 1

Buttress Size, Fabric Column and Cuff Dimensions

| Buttress Size "A" | Fabric Column Width "B" (mm) | Cuff Fabric Dimension Length "C" (mm) |
|---|---|---|
| R30 | 128 | 10 |
| R32 | 136 | 10 |

TABLE 1-continued

Buttress Size, Fabric Column and Cuff Dimensions

| Buttress Size "A" | Fabric Column Width "B" (mm) | Cuff Fabric Dimension Length "C" (mm) |
| --- | --- | --- |
| R34 | 144 | 10 |
| R36 | 152 | 10 |
| R38 | 160 | 10 |
| R40 | 168 | 10 |

The buttress 10 according to the present invention is composed of Teflon MS 010 fabric supplied by Bard of the United Kingdom. Tissue in-growth has been demonstrated to occur reliably when Teflon (Trade Mark) is used in a buttress 10 according to the invention. It will be appreciated that any suitable inert, non-degradable and sufficiently elastic (i.e. expandable and contractable) woven or knitted fabric of medical grade and supportive of tissue in-growth may be used in place of Teflon MS 010. It will also be appreciated that the elastic nature of the fabric may arise because of its mechanical structure and/or its chemical composition. A suitable fabric must, of course, be sufficiently elastic to support the damaged annulus and to permit normal (or almost normal) physiological annular movement during the cardiac cycle.

Thus, the fabric should be sufficiently elastic to permit longitudinal elongation to no more than 150%, preferably to no more than 125%, most preferably to 105–108% of its unextended length. Optionally, the fabric should also be transversely extendible, to accommodate non-planar movement of the annulus during the cardiac cycle. In addition, the fabric should be sufficiently elastic to permit the 25% increase in atrioventricular valve orifice surface area which occurs during each cardiac cycle.

Within these prescriptions, a great variety of woven or knitted fabrics may be used including fabrics derived from polytetrafluoroethylene (e.g., GoreTex (Trade Mark) and Teflon (Trade Mark)) and from polyethylene terephthalate (e.g., Dacron (Trade Mark)). The Teflon fabric sheet is placed on a designated clean work surface, "right side" up, with the ribs running directly away from the operator (ribs partially shown in FIG. 1). The operator cuts parallel with the ribs, to remove any frayed and/or partial ribs from the right hand side of the sheet. The operator then cuts a column of fabric of width "B", measuring from right to left. The appropriate column width is obtained using, for example, the dimensional information from Table 1 and the relevant measurement is marked with a straight pin. If the measurement falls in the middle of a rib, the pin is moved to the right so that the cut will be made between ribs. A slight cut is made with scissors and the pin is then removed. Cutting is then continued between the ribs from the bottom to the top of the fabric sheet, thereby separating an individual column having the width "B" from the main sheet (see FIG. 1). Further individual columns are then cut by repeating the above steps to yield the desired quantity of fabric columns.

The column of width "B" is then placed "wrong side" up, and twisted through 90°, so that the ribs are running longways, away from the operator (ribs partially shown in FIG. 2). The width of the desired cuff is measured by referring to, for example, the cuff width "C" specified in Table 1, measuring from left to right. The desired measurement is marked with a straight pin and a slight cut is made with a scissors. The pin is then removed and cutting is continued until an individual cuff has been detached from the column, ensuring at all times that cutting is between the ribs. Thus, an individual cuff having the dimensions "B"× "C" is obtained (see FIG. 2). This step is repeated to achieve the desired quantity of individual elongate members 12 in the form of cuffs. Each longitudinal end 22,22' of an individual cuff 12 is then folded back, in reflex manner, as illustrated in FIG. 3, and both longitudinal ends 22,22' of the cuff 12 are joined, wrong sides facing, 3 mm from their respective edges, by a first seam 18. The first seam 18 is made using an approximately 50 cm length of 5/0 white suture comprising, for example, Filodell coated, virgin braided polyester surgical suture having a diameter of 0.0048±0.001. A suitable suture is supplied by Purcell Sutures of the United Kingdom. The 5/0 white suture is threaded through a size 10B needle, whereupon both thread ends are joined and secured by tying a ½ overhand knot (left over right, right over left). The excess thread ends are then trimmed as close to the knot as is possible. The threaded needle is then inserted through the right side, making one back stitch (make a stitch, go back over the last stitch one more time), ensuring that the fabric ends are within the stitch. The same stitching pattern is then continued to the end of the seam, ensuring an even tension along the first seam 18. The operator should avoid pulling the thread too tight as this will cause distortion of the first seam 18. The last stitch is placed as for the first stitch, ensuring that the edge of the fabric is taken into the stitch. The needle is then passed through the loop and the thread is gently pulled until the loop closes making a loop knot, thereby securing the end. The thread is then trimmed as close to the knot as is possible. The first seam 18 is then opened and flattened with a steel ruler and excess material is trimmed off (not shown).

The first seam 18 is then positioned adjacent the transverse mid-line of the cuff 12 (see FIG. 3). An approximately 70 cm length of 5/0 white suture is threaded through a size 10B needle. Both thread ends are joined and secured by tying a ½ overhand knot and the excess thread ends are trimmed as close to the knot as is possible. To join both ends of the fabric by a second seam 14 (see FIG. 4), the threaded needle is inserted approximately 3 mm from the respective superimposed selvedges or fabric edges 24,24' and the needle is inserted through the "right side", making one back stitch ensuring that the ends are within the stitch and bringing the needle through the second seam 14 line. Stitching is continued in the same pattern until approximately one third of the second seam 14 is complete. The needle is then inserted back into the back stitch already made, making a securing stitch 26 in the second seam 14. The normal stitching pattern is then continued until approximately two thirds of the second seam 14 has been completed and, again, a securing double back stitch 26 is made. The normal stitching pattern is then continued to the end of the second seam 14, ensuring an even tension throughout. The operator should avoid pulling the thread too tight as this will cause distortion of the second seam 14. The last stitch is placed as for the first stitch, ensuring the edge of the fabric is taken into the stitch. The needle is then run back through the final back stitch making a loop in which the needle is passed through. The thread is then gently pulled until the loop closes making a loop knot and securing the end. The thread is trimmed as close to the knot as is possible. Excess material is then trimmed and the operator should check that the second seam 14 is intact and will not fray. The cuff 12 is then pulled inside-out and flattened (see FIG. 5 in which the trimmed longitudinal ends 22,22' of the first seam 18 and the trimmed fabric edges 24,24' of the second seam 14 are indicated in dotted outline).

TABLE 2

Length of Radiopaque Material and Dimensions of
Finished Buttress according to the invention

| Buttress Size "A" | Radiopaque Silicone Length "D" (mm) | Finished Buttress Width "E" (mm) | Finished Buttress Length "F" (mm) |
| --- | --- | --- | --- |
| R30 | 56 | 4.5 | 60 |
| R32 | 60 | 4.5 | 64 |
| R34 | 64 | 4.5 | 68 |
| R36 | 68 | 4.5 | 72 |
| R38 | 72 | 4.5 | 76 |
| R40 | 76 | 4.5 | 80 |

A suitable radiopaque material 20 comprises radiopaque silicone filaments having a 1.0±0.5 mm diameter, which are obtained from Speciality Silicone Fabricators, Inc.of 3077 Rollie Gates Drive, Paso Robles, Calif. 93446, United States of America under the Trade Name SSF-METN-750. Such a filament has a minimum tensile strength of 1200 p.s.i., a minimum elongation of 750% and a minimum tear strength of 200 ppi. The silicone filament is cut into the desired length (see Table 2) using a scissors, a sharp blade or the like, ensuring that an even clean cut is made, which is free from tears, punctures, etc. The silicone strip 20 is then inserted into the buttress 10 by placing it flat against the second seam 14, ensuring it is not twisted or creased (see FIG. 6 in which the radiopaque strip 20 is illustrated in dotted outline).

A third seam 16 is made using a 70 cm length of 5/0 white suture, which is threaded through a size 10B needle. A ½ overhand knot is made and excess thread is trimmed, single suture being used for this seam 16. Each of the right hand superimposed selvedges or fabric edges 28,28' of the cuff 12 are then folded inwardly to the extent necessary to ensure that the finished buttress 10 conforms to the dimensions specified in Table 2. The threaded needle is inserted, to make a back stitch. The stitches are picked up by sewing 1 mm hemming stitch on alternate sides of the seam 16. All stitches are taken in a slightly different area to prevent fatiguing of the fabric. Again, when approximately one third of the third seam 16 is stitched, a securing loop stitch 30 is made. The stitching pattern is continued, folding both sides 28,28' evenly, until approximately two-thirds of the third seam 16 is complete and, again, a securing loop stitch 30 is made. The stitching pattern is then continued to the end of the third seam 16 ensuring that the thread is not pulled too tight, so as to cause distortion of the third seam 16. Having completed the third seam 16, the operator finishes with a securing loop stitch and the needle is inserted into the corner of the cuff 12. The needle is then brought up through the flat of the cuff 12 on the same side as the first seam 18, approximately 10 mm from the edge, ensuring that the needle does not contact the silicone strip 20. A 1 mm double back stitch is made, with a loop on the last back stitch to secure the thread. The thread is then buried for another 2 mm and excess thread is clipped as close to the fabric as is possible.

An indicator (visible as 232 in FIG. 12) is attached using a 50 cm length of 5/0 green suture, which is threaded through a size 10B needle. The indicator, which may be star-shaped, is made on the first seam-less side of the cuff 12 adjacent the transverse mid-line. This is achieved by inserting the needle into the surface of the fabric making a securing back stitch approximately 10 mm from the transverse mid-line. The needle is moved to form a longitudinal stitch and a transverse stitch is then placed through the centre of the longitudinal stitch, thereby forming the "star" shape. The needle is then re-inserted in the surface of the fabric coming up approximately 10 mm on the opposite side of the indicator and a securing back stitch is made. The thread is then buried and trimmed as close as is possible to the surface of the fabric. The star indicator serves to flatten the profile of the buttress 10 adjacent the transverse mid-line since, otherwise, the buttress 10 tends to protrude due to the volume displaced by the longitudinal edges 22, 22' of the first seam 18.

In use, the buttress 10 according to the invention is sutured into the mitral annulus, with the first seam 18 adjacent the mitral annulus itself, so that the indicator faces the orifice and identifies the transverse mid-line of the buttress 10 according to the invention.

If the thread should break during any of the first, second and third seams 18, 14, 16, the cuff 12 is rejected.

When the buttress 10 according to the invention is initially formed, the buttress 10 is cuboid and, therefore, extends in a substantially rectilinear direction.

It will be appreciated that the trimmed fabric edges 24,24' of the second seam 14 and the fabric edges 28,28' of the third seam 16 each extend inwardly, facing each other, within the elongate member 12. These inwardly extending fabric edges 24,24',28,28' provide sufficient structural integrity so that the buttress 10 can, in use, support the damaged annulus so as to restore normal annular function. The buttress 10 according to the invention may be supplied in a desired arcuate shape, on a holder as described and exemplified in the following Examples 4 and 5. Alternatively, the ring may be shaped to the desired shape by moulding the buttress 10 about a mould of the desired shape (not shown), attaching sutures to the longitudinal ends 38 of the buttress 10 followed by tying the sutures in place so that the desired shape is held. The mould may then be removed.

In addition, sterilisation assists in maintaining the buttress 10 in the desired shape. It has been found that, during sterilisation, moisture is absorbed from the radiopaque material 20 and/or from the surrounding atmosphere—it is believed that this moisture absorption aids in maintaining the desired buttress 10 shape.

EXAMPLE 2

Figure 9:
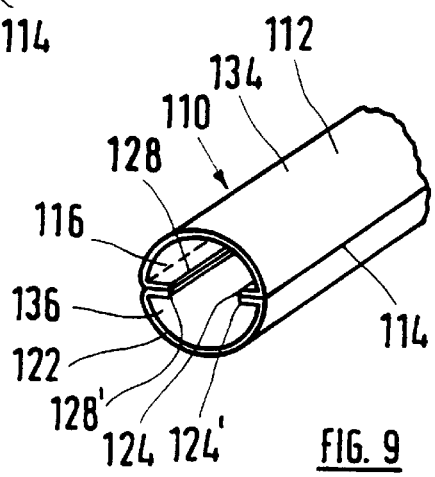

FIGS. 8 and 9 illustrate a second embodiment of a buttress 110 according to the present invention, which comprises two superimposed layers 134,136 of fabric for example Teflon felt. A suitable felt is manufactured by Meadox Medicals Incorporated of 111 Baurer Drive, Oakland, N.J. 07436, United States of America, under the Trade Mark Meadox. The fabric has been fastened or sewn together by longitudinally extending second and third seams 114,116, following which the elongate member 112 is turned inside out (see FIG. 9) using a crochet-type hook (not shown) so that the respective fabric edges 124, 124', 128, 128' of the second and third seams 114,116 extend inwardly within the elongate member 112, opposing each other, where they act as internal packing in the buttress 110 endowing it with a requisite small degree of rigidity. In order to render the buttress 110 radiopaque, the fabric of one or both layers 134,136 is impregnated with a radiopaque material.

The buttress 110 is finished off by tucking in the superimposed free ends 122 and by then forming a fourth seam (not shown) at each end 138 thereof.

EXAMPLE 3

Figure 10:
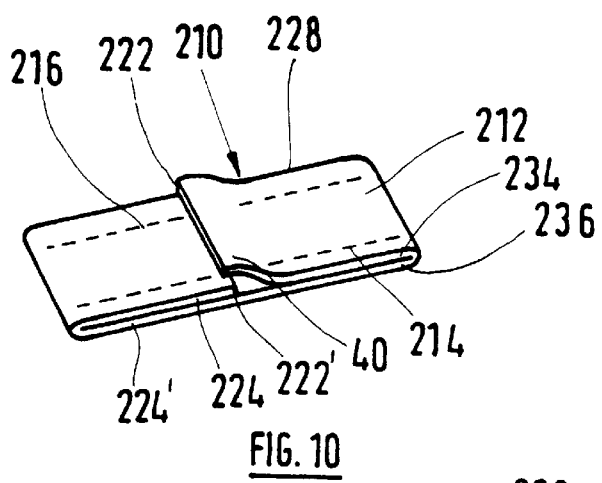
FIG. 10 is a perspective view.
Figure 11:
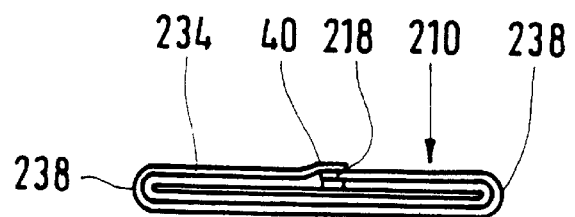
FIG. 11 is a longitudinal sectional view and FIG. 12 is a plan view of a buttress according to a third embodiment of the present invention.
Figure 12:
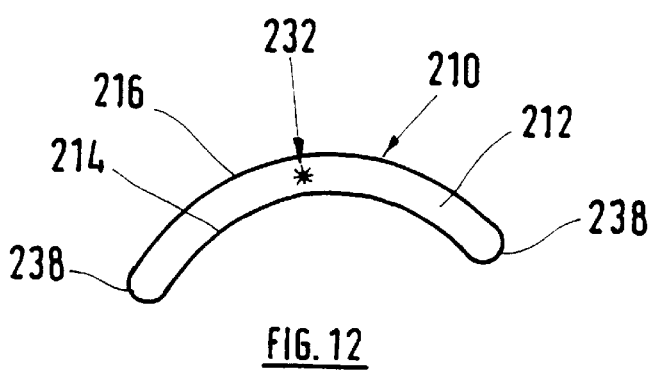

FIGS. 10–12 of the accompanying drawings illustrate a third embodiment of a buttress 210 according to the present invention.

The buttress 210 is formed from one layer of fabric, each longitudinal end 222,222' of which is folded in a reflex manner, to form the required two layers having longitudinal ends 238. The layers are then fastened together by longitudinally extending second and third seams 214,216. As in the earlier embodiments, the elongate member 212 is then turned inside out (see FIGS. 11 and 12) using a crochet-type hook (not shown) so that the respective fabric edges 224, 224', 228, 228' (fabric edge 228' not visible) of the second and third seams 214,216 now extend inwardly, opposing each other.

The ends 238 of the elongate member 212 are smooth and closed and the buttress 210 is then closed by providing a first seam 218 at a lap joint 40.

The buttress 210 can be shaped to a desired arcuate angle by shaping the buttress 210 about a mould (not shown), by suturing the free ends 238 to each other at the desired spacing (not shown) or in any other manner.

EXAMPLE 4

Assembly of a Buttress According to the Invention on a Holder

Figure 13:
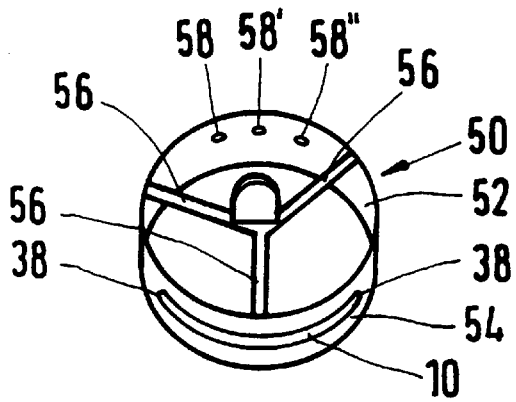
FIG. 13 is a perspective view of a first embodiment of a holder.

FIG. 13 of the accompanying drawings illustrates a first embodiment of a holder generally indicated as 50. The holder 50 comprises a circumferentially extending rim 52 having a circumferentially extending groove 54, which groove 54 extends over at least a part of the circumference of the rim 52. The groove 54 is shaped and dimensioned to accept a buttress 10, 110, 210 according to the present invention as will be described in greater detail hereinafter. A plurality of radially extending spokes 56 support the rim 52.

Circumferentially arranged apertures 58, 58', 58" are provided in the rim 52.

When it is desired to assemble a buttress according to the invention onto the holder 50, thread is fed inwardly through the aperture 58'; outwardly through the aperture 58"; through one longitudinal end 38 of the buttress 10 and thence to the other longitudinal end 38 of the buttress 10; inwardly through the aperture 58 and outwardly again through the aperture 58'. With both thread ends now in the same position, i.e. extending from aperture 58', the thread is gently pulled by an even amount on either side, to elongate the buttress 10 to the desired elongation. Four overhand knots are then made to secure the buttress 10 on the holder 50, firmly in place. The suture threads have been omitted from FIG. 13 for clarity.

FIGS. 14A–H of the accompanying drawings illustrate a second embodiment of a holder 150. The holder 150 comprises a circumferentially extending rim 152, supported by radially extending spokes 156. A circumferentially extending groove 154 is provided to receive a buttress 10, 110, 210 according to the invention.

The assembly should be performed on a designated clean work surface in a clean environment area.

A suitable holder 150 is annular and includes six apertures, A1, A2, A3, B1, B2 and B3, each extending radially through the rim 152.

The buttress 10, 110, 210 according to the present invention is assembled on the holder 150 in the following manner.

A 50 cm length of 2/0 green suture is threaded through a size 5B needle and a ½ overhand knot is made. The 2/0 green suture suitably comprises Filodell coated, virgin braided polyester surgical suture having a diameter of 0.0125±0.001. A suitable suture is supplied by Purcell Sutures of the United Kingdom. The buttress 10, 110, 210 is positioned in the groove 154, so that, from above, the buttress 10, 110, 210 is not visible and fits snugly in the groove 154. The needle is then brought in through A2 and directly through B2 (see FIG. 14B). With the buttress 10, 110, 210 in place on the holder 150, the needle is then brought through the surface fabric of the buttress 10, 110, 210 to the right of B2 (see FIG. 14C) making an approximately 1 mm stitch on the buttress 10, 110, 210. The needle is then inserted through B3 and then A3 (see FIG. 14D). The needle is then brought up through the middle of one longitudinal end 38 of the buttress 10, 110, 210 on the surface of the fabric making an approximately 1 mm stitch. The needle is then placed over the middle of the opposite longitudinal end 38 and again a 1 mm stitch is made on the surface of the fabric (see FIG. 14E). The needle is then inserted through A1 and directly through B1 (see FIG. 14F). The needle is then brought up through the surface of the fabric making a 1 mm stitch to the left of B2 (see FIG. 14G) and the needle is then brought back through B2 followed through A2 (see FIG. 14H).

With both thread ends now in the same position, i.e., extending from A2, the thread is then gently pulled an even amount on either side, ensuring that the thread is not pulled too tight as this will cause distortion. This elongates or stretches the buttress 10, 110, 210 on the holder 150 to no more than 150%, preferably no more than 125%, most preferably 105–108% of its unextended length. The operator should then ensure that the buttress 10 is secure and firmly in place and four overhand knots are then begun. Upon completion, the thread ends are cut as close to the knot as is possible.

If desired, an identification tag (not shown) may be attached to the buttress 10, 110, 210. Such an identification tag may carry a serial number. The identification tag may be attached using an approximately 50 cm length of 5/0 white suture threaded into a size 10B needle. The assembled buttress 10, 110, 210 according to the invention and holder 150 may then be placed in a pouch which can be heat sealed.

When it is desired to perform annuloplasty using a buttress according to the present invention, the buttress/holder is removed from the pouch and offered to the annulus where the buttress is sutured into place. When the buttress is secured to the annulus, the green suture connecting the buttress to the holder is severed and the green suture and the holder are discarded. Since the buttress has been offered to the posterior aspect of the annulus extended beyond its unextended length, this urges the posterior aspect to contract, thereby restoring the normal resting orifice surface area.

Alternatively, the buttress may be offered to the orifice without a holder.

EXAMPLE 5

Alternative Holders

Figure 15:
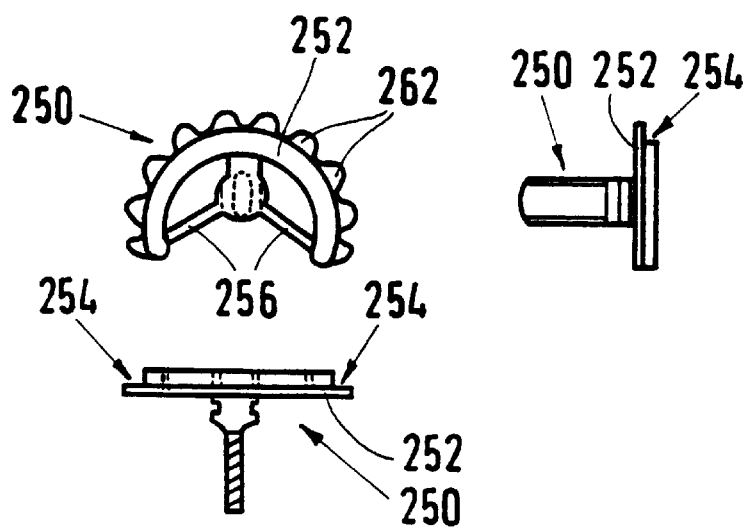
FIG. 15 is underneath, section and side views of a third embodiment of a holder.
Figure 16:
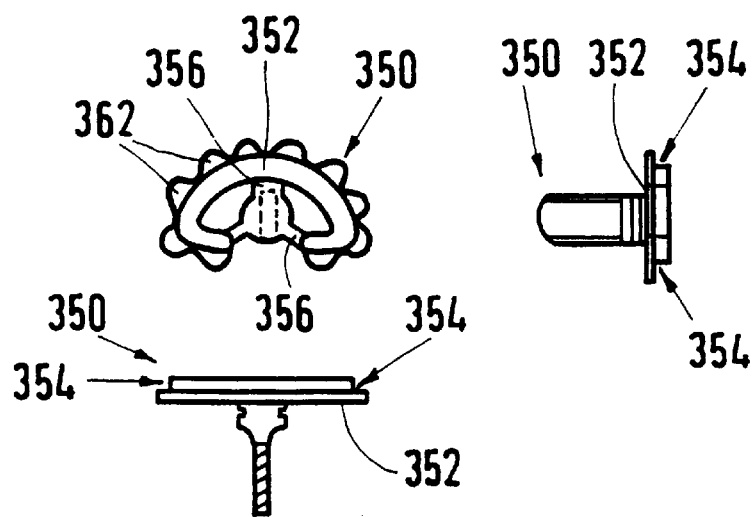
FIG. 16 is underneath, section and side views of a fourth embodiment of a holder.
Figure 14A:
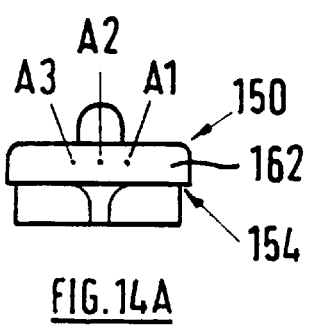
FIGS. 14A–14H are plan and end views of sequential steps in assembling a buttress according to the invention onto a second embodiment of a holder.
Figure 14B:
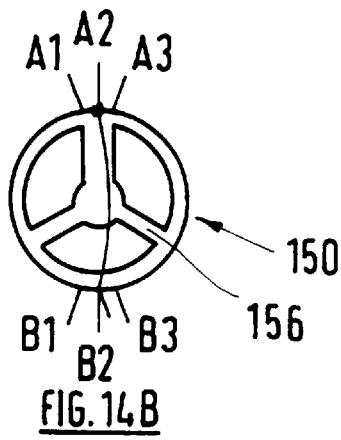
Figure 14C:
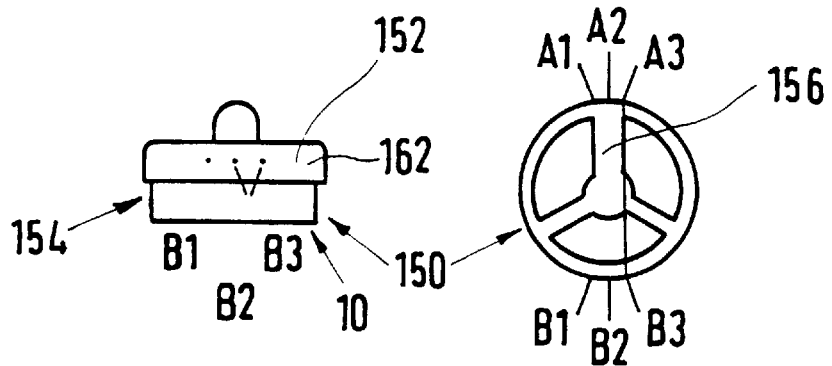
Figure 14D:
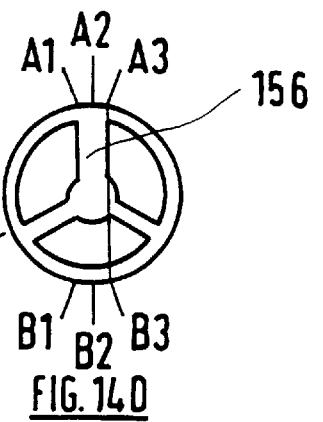
Figure 14E:
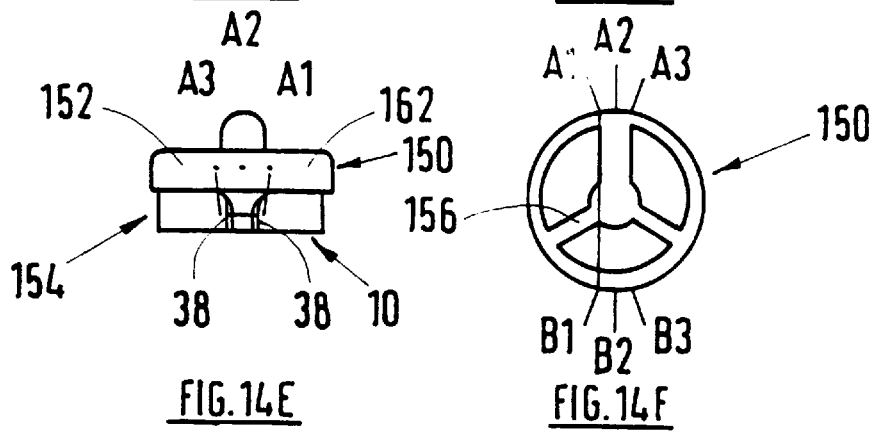
Figure 14F:
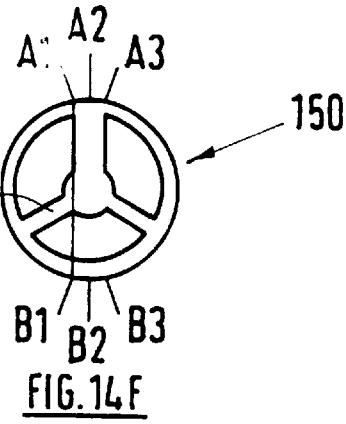
Figure 14G:
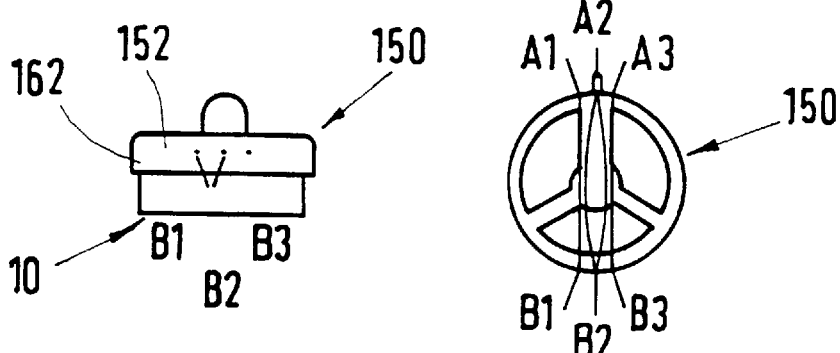
Figure 14H:
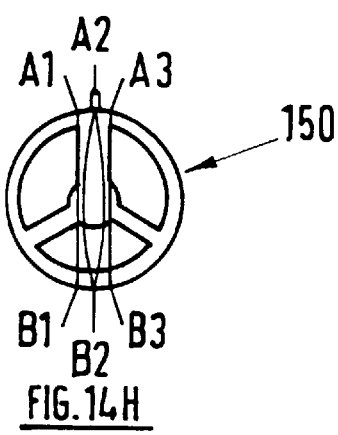

FIGS. 15 and 16 of the accompanying drawings illustrate alternative holders 250, 350. FIG. 15 illustrates plan, side and sectional views of a pen-torus-shaped holder 250 having a scalloped flange 262 extending from the rim 252 of the pen-torus. Similarly, FIG. 16 illustrates plan, side and sectional views of a pen-toroid-shaped holder 350, having a scalloped flange 362 extending from the rim 352 of the pen-toroid.

Assembly of a buttress 10, 110, 210 according to the present invention on each of these holders 250, 350 involves stitching the buttress 10, 110, 210 onto the holder 250, 350 by threading the needle through the apertures indicated in dotted outline on the respective sectional views.

In each case, the buttress 10, 110, 210 is desirably elongated on the holder 250, 350 by gently pulling the suture threads evenly, before securely tying them.

EXAMPLE 6

Mitral Valve Reconstruction 261 patients underwent mitral reconstruction by annuloplasty for mitral regurgitation from Jan. 1, 1983 to Jul. 17, 1996 and received either a Carpentier rigid closed ring, a known flexible closed ring or, alternatively, a buttress according to the present invention. The age at operation ranged from 2 months to 77 years, with a mean of 58.5 years. The aetiology of the valve disease was degenerative 122 (46.7%), rheumatic disease 71 (27.2%), ischaemic 28 (10.7%), congenital 19 (7.3%), endocarditis 18 (6.9%) and others 3 (1.1%). All of the operations were performed using cardiopulmonary by-pass and annuloplasty was performed on 258 patients, of whom 77 received a posterior mitral annuloplasty using a buttress according to the present invention, manufactured according to the procedure of Example 1 and the balance received a known (Carpentier) closed rigid ring in 146 patients or known flexible closed rings. The unextended length of the buttress according to the invention approximated four times the maximum depth of the anterior mitral leaflet, from its base to its commissure with the posterior mitral leaflet.

The overall 30 day hospital mortality was 8 of 261 patients (3%), whereas the 30 day hospital mortality for isolated mitral annuloplasty was 1 of 152 patients (0.65%). The actuarial 1 year, 5 year and 10 year survival rates were 96%, 93% and 90%, respectively. The re-operation free rates at 5 years and 10 years were 92% and 90%, respectively. There was no difference in the 30 day hospital mortality, actuarial survival rates and re-operation free rates for the 77 patients receiving a buttress according to the present invention, when compared with the 146 patients receiving a Carpentier known rigid ring.

The rigid closed ring Carpentier group of patients actuarially had an incidence of repair failure of three cases at a mean follow-up of one year. The mean follow-up for the 77 patients receiving a buttress according to the present invention is thirteen months, with two patients requiring re-operation for reconstruction failure. The ex-planted flexible buttress devices showed no technical fault, which compares most favourably with the rigid ring population.

Clinical experience suggests that mitral reconstruction by annuloplasty using a buttress 10, 110, 210 according to the present invention is a stable durable repair with low mortality and low re-operation rates. Furthermore, correct positioning in the annulus and correct elongation of the buttress 10, 110, 210 according to the present invention, is facilitated by using a holder 50, 150, 250, 350.

It has surprisingly been found that, despite the flexible nature and the non-closed nature of the buttress according to the present invention, such a buttress permits physiological annular movement and physiological expansion/contraction of the annular circumference during the cardiac cycle whilst also restoring the damaged annulus towards its normal physiological shape. It has been unexpectedly found that such flexible open rings are not associated with reduction of the orifice size of the annulus, so that stenosis is avoided. In addition, suture prolapsing has not been observed. These significant clinical and technical advantages are unexpected, in that the corresponding disadvantages have been associated with flexible closed rings and it would not have been expected that open flexible rings which, of their nature are less structurally intact, would avoid these disadvantages.

I claim:

1. A buttress for reconstructing a cardiac valve having cusps, the buttress comprising:
    two superimposed layers of a fabric forming an elongate member, the fabric partially-annularly fitting against a base of the cusps, the fabric being longitudinally extendable to 105–150% of a non-extended length of the elongate member; and,
    longitudinally extending seams for fastening the layers together, said seams having inwardly extending opposing selvedges.

2. A buttress according to claim 1, wherein free ends of the elongate member define an arcuate spacing therebetween, the arcuate spacing being more than one quarter of the non-extended length of the elongate member.

3. A buttress according to claim 1, wherein the buttress is adapted for reconstructing a mitral valve, the mitral valve having an anterior leaflet and a posterior leaflet, the leaflets meeting at a commissure; and,
    the buttress fitting against at least a base of the posterior mitral leaflet, the non-extended length approximating four times a maximum depth of the anterior leaflet from the base of the anterior leaflet to the commissure with the posterior leaflet.

4. A buttress according to claim 1, wherein the buttress is adapted for reconstructing a tricuspid valve; and,
    the buttress fitting against at least a base of an anterior leaflet of the tricuspid valve.

5. A buttress according to claim 1, wherein the fabric is extendable both longitudinally and transversely.

6. A buttress according to claim 5, wherein the fabric further comprises longitudinally extending ribs disposed on one side of the fabric and transversely extending ribs disposed on a reverse side of the fabric, whereby the ribs allow the fabric to be longitudinally and transversely extendable.

7. A buttress according to claim 1, wherein the fabric is woven or knitted from polymerized tetrafluoroethylene.

8. A buttress according to claim 1, wherein to form the two superimposed layers, the elongate member comprises a length of the fabric folded at each end of the elongate member in a reflex manner.

9. A buttress according to claim 1, wherein the elongate member comprises two superimposed lengths of fabric.

10. A buttress according to claim 1, wherein the buttress is impregnated with a radiopaque material comprising an inert, water insoluble, heavy metal compound.

11. A buttress according to claim 10, wherein the heavy metal compound is selected from the group comprising barium sulphate and titanium dioxide.

12. A buttress according to claim 1, further comprising a radiopaque filament within the buttress, the radiopaque filament including an inert, water insoluble heavy metal compound.

13. A buttress according to claim 12, wherein the heavy metal compound is selected from the group comprising barium sulphate and titanium dioxide.

14. A buttress according to claim 1, wherein the fabric is longitudinally extendable to 105–125% of the non-extended length.

15. A buttress according to claim 1, wherein the fabric is longitudinally extendable to 105–108% of the non-extended length.

16. An apparatus for cardiac valve reconstruction, the apparatus comprising:

a holder including a buttress receiving area having a partially-annular configuration;

a buttress comprising an elongate member and being of a fabric, the fabric being longitudinally extendable to an extended condition being 105– 150% of a non-extended length of the elongate member; and, mounting means for removably mounting the buttress on the buttress receiving area in the extended condition.

17. An apparatus according to claim 16, wherein respective free ends of the elongate member define an arcuate spacing therebetween, the arcuate spacing being more than one quarter of the non-extended length of the elongate member.

18. An apparatus according to claim 16, further comprising an arcuate rim providing the buttress receiving area.

19. An apparatus according to claim 18, wherein the rim includes a groove, the groove defining the buttress receiving area.

20. An apparatus according to claim 18, further comprising a scalloped flange extending from the rim and defining a buttress receiving area between the flange and the rim.

21. An apparatus according to claim 18, wherein the rim is supported by a plurality of radially extending spokes.

22. An apparatus according to claim 18, wherein the mounting means is a length of suture thread, the suture thread being removably connected to respective free ends of the buttress, and free ends of the length of the suture thread being secured, under tension, so as to stretch the buttress into the extended condition.

23. An apparatus according to claim 22, wherein the rim includes an aperture intermediate free ends of the buttress receiving area, both free ends of the suture thread extending through the aperture and being secured together, under such tension so as to stretch the buttress to the extended condition.

24. A buttress according to claim 16, wherein the fabric is longitudinally extended to 105–125% of the non-extended length.

25. A buttress according to claim 16, wherein the fabric is longitudinally extended to 105–108% of the non-extended length.

26. A method for cardiac valve reconstruction, the cardiac valve having cusps, comprising the steps of:

reversibly mounting a buttress onto a holder to form an apparatus for cardiac valve reconstruction, the buttress comprising an elongate member of a fabric, the fabric being longitudinally extended to 105–150% of a non-extended length of the elongate member;

fixing the buttress to a base of the cusps; and detaching the buttress from the holder thereby allowing the buttress to contract towards the non-extended length.

27. A buttress according to claim 26, wherein the fabric is longitudinally extended to 105–125% of the non-extended length.

28. A buttress according to claim 26, wherein the fabric is longitudinally extended to 105–108% of the non-extended length.

* * * * *

UNITED STATES PATENT AND TRADEMARK OFFICE
CERTIFICATE OF CORRECTION

PATENT NO. : 6,019,791
DATED : February 1, 2000
INVENTOR(S) : Wood

It is certified that error appears in the above-indentified patent and that said Letters Patent is hereby corrected as shown below:

Column 1, line 37, replace "20-250%" with --20-25%--.

Signed and Sealed this

Third Day of April, 2001

Attest:

NICHOLAS P. GODICI

*Attesting Officer*   Acting Director of the United States Patent and Trademark Office